United States Patent [19]

Spector

[11] Patent Number: 5,732,651

[45] Date of Patent: Mar. 31, 1998

[54] OPTICAL OBSERVATORY FOR INSECT FARM

[76] Inventor: Donald Spector, 380 Mountain Rd., Union City, N.J. 07080

[21] Appl. No.: 834,888

[22] Filed: Apr. 7, 1997

[51] Int. Cl.⁶ .......................... F21V 33/00; A01K 29/00
[52] U.S. Cl. ................................. 119/6.5; 362/138
[58] Field of Search ................... 119/6.5; 362/125, 362/138, 245, 247, 307, 328

[56] References Cited

U.S. PATENT DOCUMENTS

| | | | |
|---|---|---|---|
| 3,580,219 | 5/1971 | Stebbins | 119/6.5 |
| 3,626,902 | 12/1971 | Orfel | 119/6.5 |
| 3,687,110 | 8/1972 | Braunhut | 119/6.5 |
| 4,120,563 | 10/1978 | Stefanou | 362/138 |
| 5,633,762 | 5/1997 | Richard | 362/247 X |

Primary Examiner—Robert P. Swiatek
Assistant Examiner—Elizabeth Shaw
Attorney, Agent, or Firm—Michael Ebert

[57] ABSTRACT

A self-contained observatory making it possible for a child or other observer to view in an enlarged scale a farm of tiny insects confined within a transparent cartridge. The housing of the observatory includes an inlet to receive the cartridge which is illuminated by a light source mounted within the housing. Also mounted within the housing is a concave mirror and a lens adapted to project a real image of the illuminated farm onto the contoured surface of the mirror. The placement of the concave mirror and its radius of curvature are such as to project onto a free space in advance of the contoured surface an upright and magnified three-dimensional virtual image of the farm of living insects whereby the observer is then better able to see the physical form of each insect and to observe its activities.

7 Claims, 1 Drawing Sheet

OPTICAL OBSERVATORY FOR INSECT FARM

BACKGROUND OF THE INVENTION

1. Field of Invention

This invention relates generally to optical devices for producing enlarged images of insects, and more particularly to a self-contained optical observatory making it possible for a child or other observer to see in a magnified scale a farm of tiny insects confined within a transparent cartridge.

2. Status of Prior Art

Children are fascinated by tiny insects, such as ants and beetles. And children who wish to see the physical details of these insects more clearly will often use a magnifying glass to observe these insects. But if an insect is free to scurry or fly away, it cannot easily be observed.

This is why in a classroom study of insects, one does not use live insects, but insect specimens which are mounted. Then one is able to observe the mounted insect under a microscope or by means of a magnifying glass.

Thus the Smith U.S. Pat. No. 3,656,848 shows a magnifying viewer in which an insect specimen is mounted on a piston whose shaft terminates in a knob, the piston being slidable within a cylindrical case having a lens supported at one end. By pushing the piston toward or away from the lens, the specimen can be brought into focus to provide a magnified view of the specimen.

The drawback to this optical viewer is that one is not able to observe a live insect and its activity, but only an inanimate specimen. This same drawback exists in the optical exhibition device shown in the Livermore U.S. Pat. No. 925,209 in which a specimen of a fish immersed in water in a transparent tank is observed through a magnifying lens.

Inasmuch as an observatory in accordance with the invention for viewing live insects makes use of a concave mirror, of background interest is the advertising display device disclosed in the Mizumo U.S. Pat. No. 4,776,118 for displaying in space an image of a product for sale by means of a concave mirror.

SUMMARY OF INVENTION

In view of the foregoing, the main object of this invention is to provide a self-sufficient optical observatory that makes it possible for a child or other observer to view in an enlarged scale a farm of tiny insects.

By an insect farm is meant a group of small insects which may be of different types held within a confined area. However, an observatory in accordance with the invention is useable for viewing a single, relatively large insect.

Among the advantages of the invention are the following:

A. What is seen by an observer is not an inanimate specimen, but a living insect whose magnified form renders visible the activities as well as the physical structure of the insect;

B. The insects available for observation are those confined within a transparent cartridge provided with a removable cover or hatch. Hence the user of the observatory is free to change the population of the insect farm;

C. The observatory is not only useful for the study of insects for it also acts as an entertaining display of insect activity. Though a tiny insect usually appears to be innocuous, when a greatly magnified virtual image of this insect is produced by the observatory, the insect assumes a monster-like fearful appearance.

To give a simple analogy, a relatively small iguana or other lizard having spiny projections on its back would, if greatly magnified, assume a dinosaur-like appearance.

More particularly, an object of this invention is to provide a self-contained optical observatory that is inexpensive to manufacture and simple to operate, for all a user need do is to insert into an inlet in the observatory housing a farm insect cartridge, and then switch on the light source illuminating the insect farm.

Briefly stated, these objects are attained by a self-contained observatory making it possible for a child or other observer to view in an enlarged scale a farm of tiny insects confined within a transparent cartridge. The housing of the observatory includes an inlet to receive the cartridge which is illuminated by a light source mounted within the housing. Also mounted within the housing is a concave mirror and a lens adapted to project a real image of the illuminated farm onto the controlled surface of the mirror.

The placement of the concave mirror and its radius of curvature are such as to project onto a free space in advance of the contoured surface an upright and magnified three-dimensional virtual image of the farm of living insects whereby the observer is then better able to see the physical form of each insect and to observe its activities.

BRIEF DESCRIPTION OF DRAWING

For a better understanding of the invention as well as other objects and further features thereof, reference is made to the following detailed description to be read in conjunction with the accompanying drawings, wherein.

DESCRIPTION OF INVENTION

Figure 1:
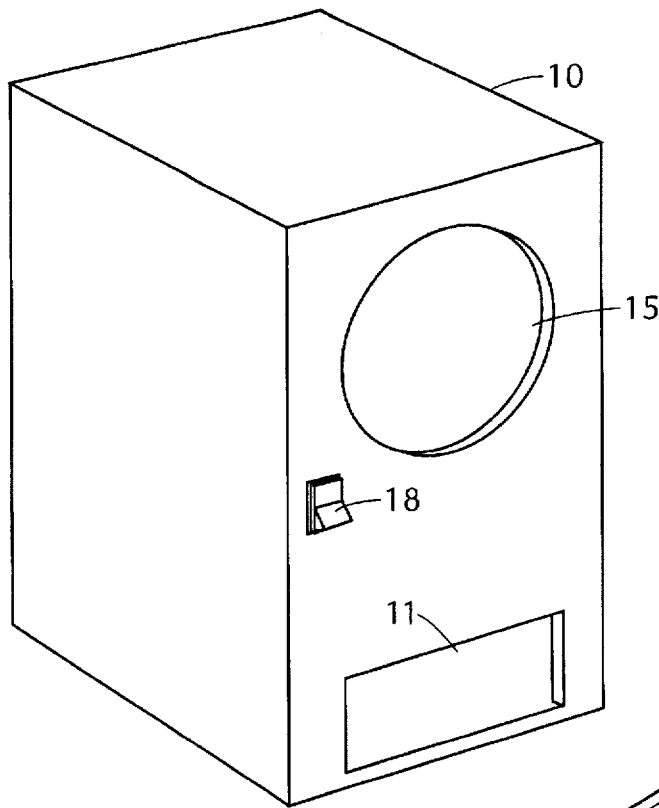
FIG. 1 is a perspective view of an optical observatory for an insect farm in accordance with the invention.
Figure 2:
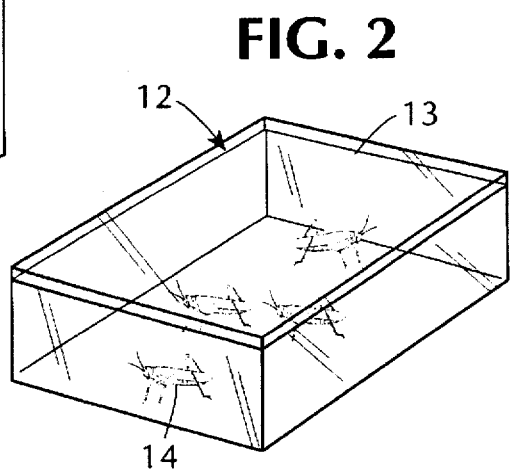
FIG. 2 illustrates the cartridge in which the insect farm is confined.

An optical observatory in accordance with the invention includes, as shown in FIG. 1, a box-like molded plastic housing 10 having at the lower end of its front panel an inlet 11 adapted to receive a rectangular cartridge 12 which is accommodated at the bottom of the housing. Cartridge 12, as shown in FIG. 2, is formed of a rectangular case of transparent synthetic plastic material, such as an acrylic of high transparency, having a removable hatch cover 13.

The case is loaded with tiny living insects 14 to create an insect farm. The insects may be those locally available, such as beetles, ants and grasshoppers. It is for the user of the observatory to decide on the composition of the insect farm. And in practice, to insure long term survival of the confined insects, the case is provided with vent holes on its sides. Also insect food and water may be provided in tiny cups placed within the cartridge.

Housing 10 is also provided at its upper end with a front circular port 15 through which is projected into space a virtual image of the insect farm.

Figure 3:
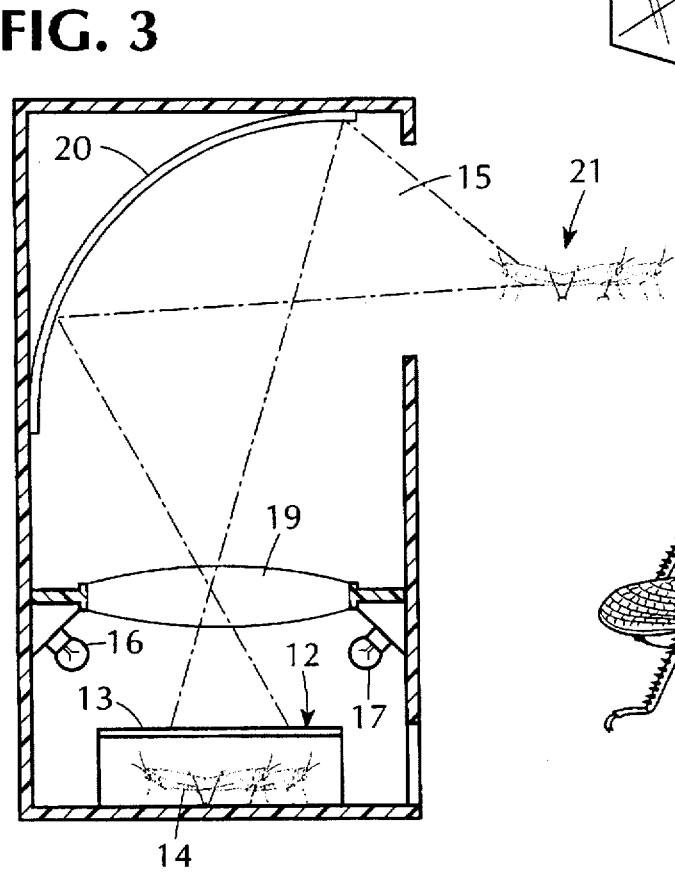
FIG. 3 schematically shows the components which make up the optical observatory.

As shown in FIG. 3, the observatory includes a pair of battery-powered lamps 16 and 17 controlled by a switch 18 mounted on the front panel of the housing, as shown in FIG. 1. (The batteries are not shown.) When the lamps are turned on to illuminate the insect farm, an illuminated real image of the insects 14 is projected by a convex lens 19 mounted within the housing above its inlet onto the contoured reflecting surface of a concave mirror 20. Mirror 20 is mounted on the upper end of the housing adjacent its side opposite circular port 15.

The bottom wall of casing 10 is preferably black and non-reflective. Since cartridge 12 is transparent, all that is projected by lens 19 onto the concave mirror 20 are images of the illuminated insects 14.

An image seen in a reflecting surface is said to be a real image when the rays reflected by this surface actually pass through points in the image. A virtual image is produced when the rays have to be traced back so that they only appear to come from the reflecting surface.

In a plane mirror, if a beam of rays emanating from an object is reflected by this mirror, the rays will change their direction, but after doing so the rays will continue on their divergent paths. Because the rays do not converge, they cannot form a real image. The rays reflected in a plane mirror therefore appear to come from a point located behind the mirror, that is from a virtual image of the object seen by the mirror. This virtual image behind the plane mirror is therefore the same distance from its reflective surface as is the object in front of the mirror.

A rear view mirror in an automobile is often a convex mirror which forms a virtual image of reduced scale having a wide field of vision behind the vehicle. The present invention makes use of a concave mirror 20 whose characteristics are similar to those of a concave shaving mirror. In a shaving mirror, when the face of the shaver comes within the focal distance of the mirror, then the shaver sees an upright and enlarged virtual image of his face. The focal distance of a concave mirror is the distance from its focal point to its principal point at the intersection of the optical axis with the principal plane.

Hence the rays of the image of the illuminated insects projected by lens 19 onto the contoured surface of concave mirror 20 are projected through outlet port 15 into a free space 21 in advance of this surface to produce an upright magnified three-dimensional virtual image of the insects populating the cartridge farm.

Figure 4:
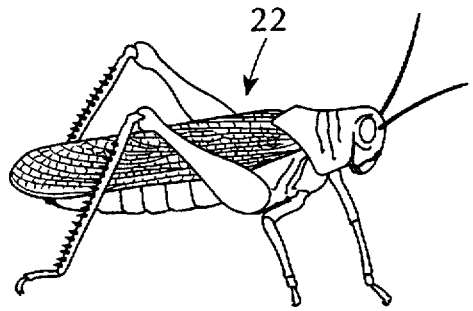
FIG. 4 shows a virtual image of an insect produced in space by the observatory.

A virtual image in space of an insect, such as the magnified image of a grasshopper 22 shown in FIG. 4, not only reveals to an observer the details of the insect, but it also shows the activities being carried out by the insect, particularly since the insect is likely to try to escape from the cartridge. And a magnified image of a tiny insect is far more impressive than a direct view of the insect, for the magnified image in free space causes the insect to assume a monster-like form. The extent of magnification can be predetermined, for it depends on the radius of curvature of the concave mirror.

While there has been shown and described a preferred embodiment of an optical observatory for an insect farm in accordance with the invention, it will be appreciated that many changes and modifications may be made therein without, however, departing from the essential spirit thereof.

I claim:

1. An optical observatory making it possible for a child or other observer to view a magnified image of at least one tiny insect; said observatory comprising:

A. a concave mirror having a contoured reflective surface;

B. means to illuminate the insect to be observed; and

C. lens means to project an image of the illuminated insect onto the contoured reflective surface to cause this surface to project into a free space in advance thereof a magnified three-dimensional virtual image of the insect.

2. An observatory as set forth in claim 1, further including a cartridge of transparent plastic material in which the insect is confined, said cartridge being exposed to a light source to illuminate the insect.

3. An observatory as set forth in claim 2, in which the cartridge has a removable cover whereby the cartridge may be loaded with desired insects.

4. An observatory as set forth in claim 2, including a housing having an inlet at a lower end thereof to admit said cartridge, and a battery-operated light source in the housing to illuminate the insect confined in the cartridge.

5. An observatory as set forth in claim 4, in which said concave mirror is mounted at an upper end of the housing which is provided with a circular port from which the virtual image is projected.

6. An observatory as set forth in claim 5, in which said lens means is a convex lens mounted in said housing above the inlet thereto.

7. An observatory as set forth in claim 2, in which the cartridge is loaded with different insects to provide an insect farm.

* * * * *